(12) United States Patent  (10) Patent No.: US 8,989,457 B2
Wiets  (45) Date of Patent: Mar. 24, 2015

(54) ANGIOGRAPHIC EXAMINATION METHOD

(71) Applicant: Siemens Aktiengesellschaft, Munich (DE)

(72) Inventor: Michael Wiets, Erlangen (DE)

(73) Assignee: Siemens Aktiengesellchaft, München (DE)

( * ) Notice: Subject to any disclaimer, the term of this patent is extended or adjusted under 35 U.S.C. 154(b) by 146 days.

(21) Appl. No.: 13/627,180

(22) Filed: Sep. 26, 2012

(65) Prior Publication Data

US 2013/0083985 A1   Apr. 4, 2013

(30) Foreign Application Priority Data

Sep. 29, 2011 (DE) .......................... 10 2011 083 704

(51) Int. Cl.
*G06K 9/00* (2006.01)
*A61B 6/00* (2006.01)
*A61B 5/02* (2006.01)
*A61B 5/00* (2006.01)
*A61B 5/0402* (2006.01)

(52) U.S. Cl.
CPC ................. *A61B 6/504* (2013.01); *A61B 6/487* (2013.01); *A61B 6/5217* (2013.01); *A61B 6/541* (2013.01); *A61B 5/02007* (2013.01); *A61B 5/7292* (2013.01); *A61B 5/0402* (2013.01)
USPC ........................................ 382/123; 382/130

(58) Field of Classification Search
USPC .................................................. 382/128, 130
See application file for complete search history.

(56) References Cited

U.S. PATENT DOCUMENTS

| | | | |
|---|---|---|---|
| 7,500,784 B2 | 3/2009 | Grebner | |
| 8,170,307 B2* | 5/2012 | Karmonik et al. | ............ 382/128 |
| 2003/0187350 A1* | 10/2003 | Omiya | .......................... 600/428 |
| 2007/0038061 A1* | 2/2007 | Huennekens et al. | ......... 600/407 |
| 2009/0067568 A1* | 3/2009 | Hall et al. | ........................... 378/4 |
| 2010/0074504 A1* | 3/2010 | Bruijns et al. | ................ 382/132 |
| 2011/0112402 A1* | 5/2011 | Yokota et al. | ................. 600/443 |
| 2012/0232387 A1* | 9/2012 | Miyachi | ........................ 600/438 |

FOREIGN PATENT DOCUMENTS

| | | |
|---|---|---|
| DE | 102007018749 A1 | 12/2007 |
| DE | 102008047825 A1 | 4/2010 |
| DE | 102009010291 A1 | 5/2010 |

\* cited by examiner

*Primary Examiner* — Matthew Bella
*Assistant Examiner* — Julian Brooks

(57) ABSTRACT

An angiographic examination method of an examination object for determining the morphology, histology and/or state of moving walls of vessels is disclosed. A series of angiography images of a section of interest of a vessel is disclosed. A quantitative analysis of the vascular wall of the section of the vessel is provided. The inherent motion of the vascular wall from two consecutive angiography images in each instance is calculated. The difference of the inherent motion of the vascular wall is visualized and/or the morphology and/or histology of the vascular wall is visualized.

16 Claims, 4 Drawing Sheets

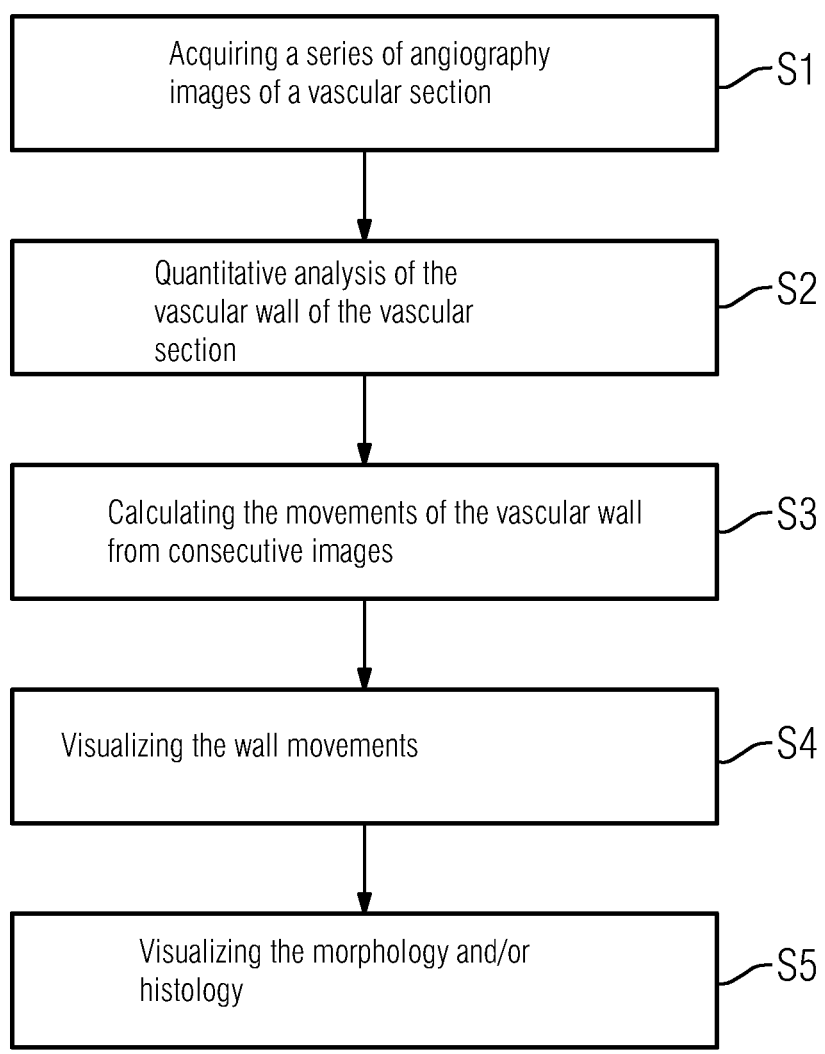

ANGIOGRAPHIC EXAMINATION METHOD

CROSS REFERENCE TO RELATED APPLICATIONS

This application claims priority of German Patent Office application No. 10 2011 083 7043 filed Sep. 24, 2011. All of the applications are incorporated by reference herein in their entirety.

FIELD OF INVENTION

The disclosure relates to an angiographic examination method of an examination object for determining the morphology, histology and/or state of moving walls of vessels.

SUMMARY OF INVENTION

An examination method of this type may be used in an x-ray diagnostic facility for instance, which is known from U.S. Pat. No. 7,500,784 B2 and is described below with the aid of FIG. 1.

FIG. 1 shows as an example a monoplanar x-ray system having a C-arm 2 held by a stand 1 in the form of a six-axle industrial or articulated arm robot, to the ends of which are attached an x-ray radiation source, for instance an x-ray emitter 3 having an x-ray tube and collimator, and an x-ray image detector 4 as an image recording unit.

By means of the articulated arm robot known for instance from U.S. Pat. No. 7,500,784 B2, which preferably has six axes of rotation and thus six degrees of freedom, the C-arm 2 can be adjusted in any spatial manner, for instance by being rotated about a center of rotation between the x-ray emitter 3 and the x-ray image detector 4. The angiographic x-ray system 1 to 4 can be rotated in particular about centers of rotation and axes of rotation in the C-arm plane of the x-ray image detector 4, preferably about the center point of the x-ray image detector 4 and about the axes of rotation intersecting the center point of the x-ray image detector 4.

The known articulated arm robot comprises a base frame, which is fixedly mounted on a base for instance. A horizontal rotating table is fastened thereto in a manner so as to rotate about a first axis of rotation. A robot rocker is attached to the horizontal rotating table so as to be pivotable about a second axis of rotation, to which horizontal rotating table a robot arm is fastened so as to be rotatable about a third axis of rotation. A robot hand is attached to the end of the robot arm in a manner so as to be rotatable about a fourth axis of rotation. The robot hand comprises a fastening element for the C-arm 2, which can be pivoted about a fifth axis of rotation and can be rotated about a sixth axis of rotation which runs at right angles thereto.

The realization of the x-ray diagnostics facility is not dependent on the industrial robot. Conventional C-arm devices can also be used.

The x-ray image detector 4 may be a rectangular or square 2-dimensional semiconductor detector, which is preferably made of amorphous silicon (a-Si). Integrating and possibly counting detectors can however also be used for instance in CMOS technology. The use of previously conventional x-ray image amplifier television networks is also possible.

A patient 6 to be examined, as an examination object, is located in the radiation path of the x-ray emitter 3 on a table plate 5 of a patient support couch. A system control unit 7 having an imaging system 8 is connected to the x-ray diagnostic facility, said imaging system 8 receiving and processing the image signals of the x-ray image detector 4 (control elements are not shown for instance). The x-ray images can then be observed on displays of a monitor lighting system 9.

Instead of the x-ray system shown in FIG. 1 for instance having the stand 1 in the form of the six-axle industrial or articulated arm robot, any angiographic x-ray system can be used, for instance also one comprising a normal ceiling or floor-mounted bracket for the C-arm 2.

Instead of the C-arm 2 shown by way of example, the angiographic x-ray system can also comprise separate ceiling and/or floor-mounted brackets for the x-ray emitter 3 and the x-ray image detector 4, which are electronically rigidly coupled for instance.

Sensors 10 which are applied to the chest of the patient 6 for instance can acquire the EKG signals of the patient 6 and relay them to a processing circuit 11 in the system control unit 7. The EKG signals of the patient 6 can however also be tapped intracardially by means of an EKG catheter (not shown).

Vessels, for instance coronary arteries, but also other vessels, were previously shown during interventional procedures in a 2D and/or 3D representation. This takes place by injecting contrast agent during an x-ray examination (angiography). The physician can conclude the pure morphology of the vessel from this examination, but not however the state of the vascular wall. Furthermore, stenoses or aneurysms can be detected and subsequently treated.

More and more methods such as for instance OCT (optical coherence tomography or FFR (fractional flow reserve) are being established and used to determine the characteristics of the vascular walls and subsequently to treat the patient in the best possible manner. The wall state of the vessel can then be determined for instance by means of IVUS (intravascular ultrasound) and/or IVUS-VH (virtual histology).

A second examination nevertheless indicates an additional burden for the patient, an additional load in terms of dose for the physician and patient and significant additional costs for the healthcare system.

To determine the morphology, histology and/or the state of vessels, a combination of x-ray and additional methods must always be used.

Alternatively, the morphology and state of the vascular wall may be concluded by means of other imaging methods such as CT and/or MR, but the angiography nevertheless is also deemed to be the gold standard in terms of imaging.

Moreover, further treatment will continue to take place in the heart catheter or angiography laboratory.

The disclosure is based on the object of easily enabling a representation of the morphology, histology and/or the state of vessels by means of just one diagnostic facility.

The object is achieved for an examination method of the type cited in the introduction by the features specified in the independent claims The object is achieved for an angiographic examination method with the following steps.
S1 Acquiring a series of angiography images of a section of a vessel of interest,
S2 Quantitative analysis of the vascular wall of the section of the vessel,
S3 Calculating the inherent motion of the vascular wall from two consecutive angiography images in each instance in respect of the expansion and/or contraction and
S4 Visualizing the difference in the inherent motion of the vascular wall.

As a result, the examining person is shown a monitor image, from which he/she may easily identify the state of the examined vessel.

According to the disclosure, the morphology and/or histology of the vascular wall may be visualized in a fifth step S5.

The calculation of the movements of the vascular walls is more accurate when the acquisition of the angiography images is implemented by way of at least one EKG cycle in accordance with step S1.

Determination of the movements of the vascular walls may be improved, if the acquisition of the angiography images takes place with a high image refresh rate, for instance with 25/30 Hz, in accordance with step S1.

To reduce the motion blurs, the acquisition of the angiography images may be implemented with short x-ray pulses, for instance with a duration of 6 to 12 ms, in accordance with step S1.

The angiography images acquired in accordance with step S1 may be fluoroscopy images or subtraction images.

The calculation of the inherent motion of the vascular wall may be implemented in accordance with step S3 by determining the difference between the maximum extension and minimum contraction of the vascular wall.

The visualization of the inherent motion of the vascular wall may take place by means of arrows corresponding to the size of the inherent motion in accordance with step S4. Alternatively, the visualization of the inherent motion of the vascular wall may take place by means of markers corresponding to the extent of the inherent motion in accordance with step S4. The visualization of the inherent motion of the vascular wall may take place by means of a color marker corresponding to the extent of the inherent motion in accordance with step S4, wherein by way of example green and red may indicate an intact and a critical vascular wall in each instance.

The vessel to be examined may be an artery, in particular the aorta for instance.

The acquisition of the angiography images in accordance with step S1 may take place by means of an x-ray system. For example, an apparatus for creating rotation angiographies for soft tissue representation, such as by means of DynaCT®, for instance in 3D.

In order to acquire the angiography images in accordance with step S1, 2D series may be created or a 3D reconstruction may be generated from at least two 2D projections.

BRIEF DESCRIPTION OF THE DRAWINGS

The disclosure is now explained in more detail with the aid of exemplary embodiments shown in the drawing, in which:

FIG. 4 shows an alternative representation of the wall movements of the vascular section and FIG. 5 shows method steps of an angiographic examination method.

DETAILED DESCRIPTION OF INVENTION

Figure 1:
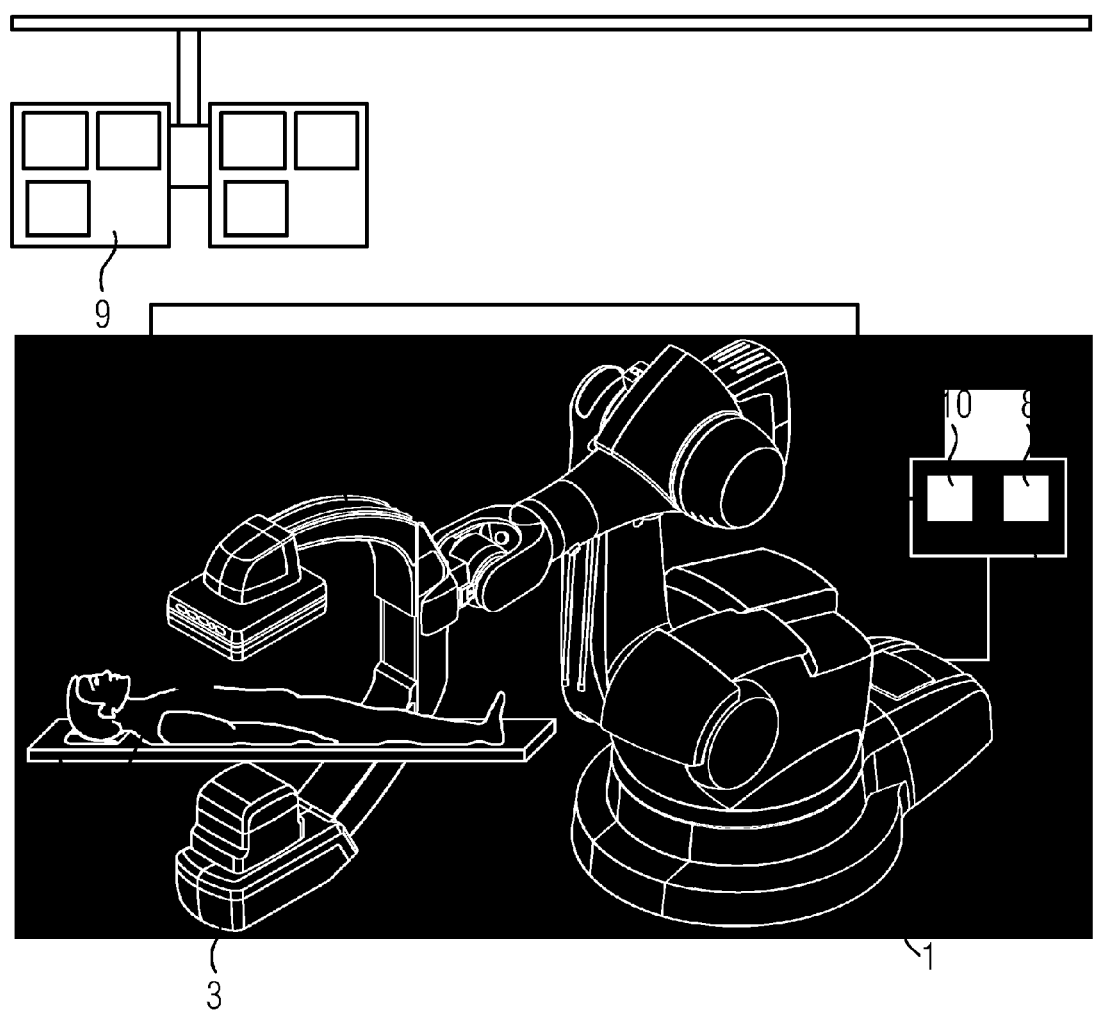
FIG. 1 shows a known C-arm angiography system having an industrial robot as a supporting apparatus.
Figure 2:
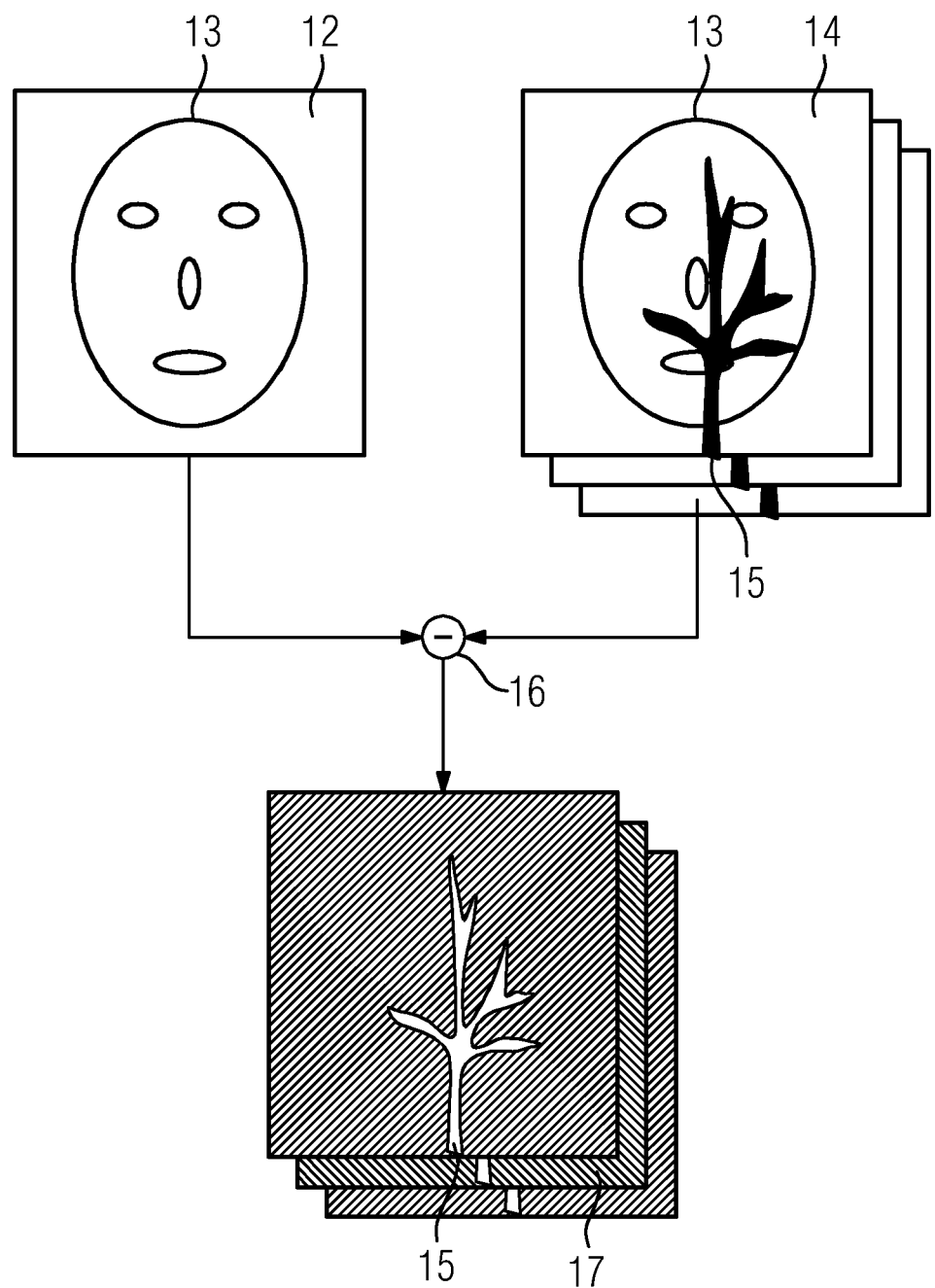
FIG. 2 shows a known DSA method (state-of-the-art)

In a known DSA method shown for instance in FIG. 2 (digital subtraction angiography), a pure native image 12 (only anatomy) with for instance a cranium 13 as a so-called mask image and an image series 14 of native images are generated using fluoroscopy from the entire filling phase, in which a vascular tree 14 is filled with contrast agent. The image series 14 of the fluoroscopy images, in which the cranium 13 and the contrast agent-filled vascular tree 15 may be seen, and the native image 12 or mask image are subtracted from one another in a subtraction stage 16. Further image processing steps such as contrast setting, edge enhancement, etc. may take place until a current image sequence 17 of subtraction images is obtained, in which only the vascular tree 15 may still easily be seen, wherein the representation usually takes place such that the vascular tree 15 appears to be light compared with the dark background.

Figure 3:
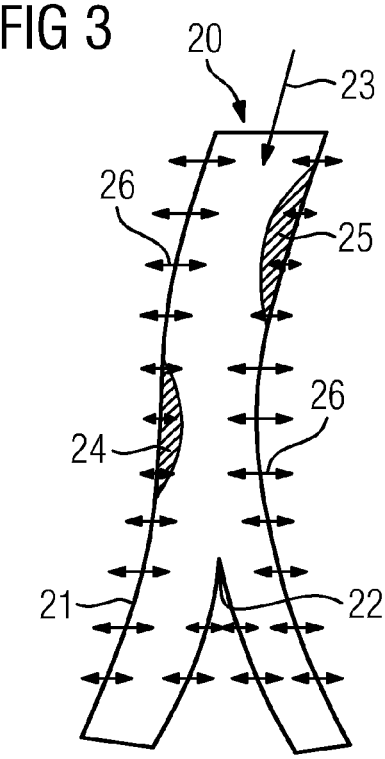
FIG. 3 shows a vascular section with its wall movements.

FIG. 3 now shows a vascular section 20 of the vascular tree 15 for instance as the object to be examined having a vascular wall 21, which has a bifurcation 22. The direction of the blood flow 23 and if necessary of the contrast agent flow is characterized by an arrow. The vascular section 20 comprises a calcification 24 for instance and a plaque 25, for instance cholesterol, which result in a stiffening of the vascular wall 21 in these affected areas, while the remaining parts of the vascular wall 21 have their normal flexibility. This is illustrated by double arrows, which render the wall movements 26 visible. These wall movements 26 are partly equal to zero in the area of the calcification 24 and the plaque 25, while in the remaining areas outside of the affected locations, they are at their maximum, such as is illustrated by the different lengths of the double arrows.

Figure 4:
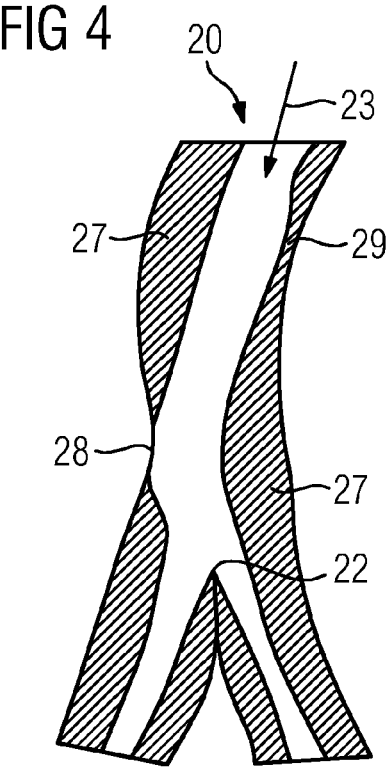

FIG. 4 shows a further type of visualization. Based on the vascular section 20 shown in FIG. 3, the wall movements 26 shown there as double arrows are visualized as markers of the inherent motions 27 of the vascular wall 21 identifying the difference between the maximum expansion and minimum contraction The minima of the difference, i.e. the areas of narrow points of the marker of the inherent motions 27 identify the site 28 of the calcification 24 and the position 29 of the plaque 25.

The object to be examined may, as shown by way of example with the aid of FIGS. 2 to 4, be the vascular section 20 of the vascular tree 15, but may however also be generally an artery, in particular the aorta.

The procedure is now shown and described in more detail in FIG. 5. In a first step S1, a series 14 or 17 of angiography images 14 or 17 of a vascular section 20 of interest in a vessel 15 is acquired. It should be noted here that the acquisition takes place at least by way of an EKG cycle having the highest possible image refresh rate and the shortest possible pulses. The angiography images 14 or 17 then have an adequately good quality in terms of a further and complete calculation of the inherent motions 26 or 27 of the vascular wall 21.

A quantitative vessel analysis of the vascular wall 21 of the vascular section 20 of the vessel is then implemented in accordance with a second step S2, by means of which the morphology, histology and/or the state of vessels, above all the vascular wall, may be determined and displayed.

In accordance with a third step S3, the inherent motions 26 or 27 of the vascular wall 21 are calculated from two consecutive angiography images 14 or 17 in each instance, wherein the differences between the maximum expansion and minimal contraction of the vascular wall 21 are determined for instance for several points on the vascular wall 21.

A visualization of the differences between the inherent motions 26 or 27 of the vascular wall 21 takes place in a fourth step S4. This may take place for instance by means of the double arrows, which, in accordance with FIG. 3, identify the extent of the wall movements 26 by means of their length. Alternatively, the visualization of the inherent motion 26 or 27 of the vascular wall 21 may take place in accordance with step S4 by the markers corresponding to the extent of the inherent motion 27. These markers or double arrows may be shown in color, wherein green and red may indicate an intact and a critical vascular wall in each instance.

According to a fifth and last step S5, the morphology and/or histology of the vascular wall 21 may be visualized.

The time-resolved representation (2D+time and/or 3D+time) of vessels enables the morphology, histology and/or state of the vascular wall to be determined simultaneously in an angiography examination.

The effect of the so-called "biological air vessel function" is exploited by the method. The so-called "physiological air vessel" consists of expanding and then constricting the wall of arteries close to the heart, above all the aorta or large arteries. The heart expels blood in the systole, while the blood flow comes to a stop in the diastole. The air vessel arteries expand during the systole, the phase of driving out blood by contracting the heart muscle, and thus also receive part of the stroke volume, which, in the diastole, the relaxation of the heart muscle, is passively contracted, thereby reducing the significant pressure difference between the systole and diastole.

The vascular diameter therefore varies with each pulse beat. This small variation is determined and displayed. Regions which are stenotic on account of a calcification, are to have less or even no variation compared with regions which have no stenosis.

This may be compared with the heart muscle, which, in the case of a heart muscle, is partially necrotic. A factor to be used in the so-called "quantitative detection of regional wall movements" during an examination of the left ventricle. In the area of the necrotic heart muscle tissue, almost no inherent motion can be identified (for instance akinesia). It is therefore possible to conclude that the coronary vessel which supplies this part of the myocardium is stenotic.

For implementation, the angiography images 14 or 17 of the vascular section of interest are recorded by way of at least one EKG cycle with the highest possible image refresh rate and the shortest possible pulses in order to reduce the motion blurs. With standard applications of the quantitative vascular analysis, the morphology and/or histology, above all the vascular wall, may subsequently be determined and displayed. The inherent motion (expansion and/or contraction) of the vascular wall is now calculated from two consecutive images in each instance. This delta of movement is subsequently visualized for further evaluation.

The time-resolved representation of vessels enables the morphology, histology and/or state of the vascular wall to be determined at the same time in the angiography examination. In this way both the dose and also the outlay in terms of time and costs may be drastically reduced. A further examination method such as IVUS, IVUS-VH, OCT, FFR, etc. may likewise be dispensed with, thus avoiding the additional x-ray exposure for examiner and patients for navigation of the additional methods with guide wires and/or catheters.

While specific embodiments have been described in detail, those with ordinary skill in the art will appreciate that various modifications and alternative to those details could be developed in light of the overall teachings of the disclosure. For example, elements described in association with different embodiments may be combined. Accordingly, the particular arrangements disclosed are meant to be illustrative only and should not be construed as limiting the scope of the claims or disclosure, which are to be given the full breadth of the appended claims, and any and all equivalents thereof. It should be noted that the term "comprising" does not exclude other elements or steps and the use of articles "a" or "an" does not exclude a plurality.

The invention claimed is:

1. An angiographic examination method of an examination object for determining an area of calcification or plaque on a vascular wall, comprising:
   acquiring a series of angiography images of a section of interest of a vessel;
   calculating a moving length between a maximum expansion and minimal contraction of the vascular wall for several points on the vascular wall from two consecutive angiography images in each instance; and
   displaying the moving length of the vascular wall for the several points on the vascular wall; and
   identifying the area of calcification or plaque on the vascular wall having a less moving length.

2. The angiography examination method as claimed in claim 1, wherein the acquisition of the angiography images is implemented according by way of at least one EKG cycle.

3. The angiography examination method as claimed in claim 1, wherein the acquisition of the angiography images takes place with a high image refresh rate.

4. The angiography examination method as claimed in claim 1, wherein the acquisition of the angiography images is implemented with short x-ray pulses.

5. The angiography examination method as claimed in claim 1, wherein the angiography images acquired are fluoroscopy images or subtraction images.

6. The angiography examination method as claimed in claim 1, wherein the moving length of the vascular wall is displayed by double arrows.

7. The angiography examination method as claimed in claim 1, wherein the moving length of the vascular wall is displayed by markers.

8. The angiographic examination method as claimed in claim 1, wherein the moving length of the vascular wall is displayed by colored arrows or colored markers.

9. The angiographic examination method as claimed in claim 1, wherein the are of calcification or plaque on the vascular wall is identified by red arrows or red markers.

10. The angiographic examination method as claimed in claim 1, wherein the vessel to be examined is an artery, in particular the aorta for instance.

11. The angiographic examination method as claimed in claim 1, wherein the acquisition of the angiography images takes place by means of an x-ray system.

12. The angiographic examination method as claimed in claim 1, wherein the acquisition of the angiography images takes place by means of an apparatus for creating rotation angiographies for soft tissue representation.

13. The angiographic examination method as claimed in claim 1, wherein the acquisition of the angiography images takes place in 3D.

14. The angiography examination method as claimed in claim 1, wherein 2D series are created in order to acquire the angiography images.

15. The angiography examination method as claimed in claim 1, wherein a 3D reconstruction is generated in order to acquire the angiography images from at least two 2D projections.

16. The angiography examination method as claimed in claim 1, wherein an intact area on the vascular wall without the calcification or plaque is identified by green arrows or green markers.

* * * * *